United States Patent
Björk et al.

[11] Patent Number: 5,658,910
[45] Date of Patent: *Aug. 19, 1997

[54] NICOTINIC ACID ESTERS

[75] Inventors: Anders Björk, Bjärred; Gunnar Andersson; Catarina Ludwig, both of Lund; Elisabeth Seifert, Kävlinge; Arne Nilsson, Malmö ; Torbjörn Lundstedt, Löddehöpinge; Lisbeth Abramo, Bjärred; Göran Pettersson, Hjärup; Curt Nordvi, Malmö ; Jin Chang Wu, Frölund, all of Sweden

[73] Assignee: Pharmacia AB, Stockholm, Sweden

[ * ] Notice: The term of this patent shall not extend beyond the expiration date of Pat. No. 5,565,455.

[21] Appl. No.: 362,475

[22] PCT Filed: Jun. 23, 1993

[86] PCT No.: PCT/SE93/00565

§ 371 Date: May 3, 1995

§ 102(e) Date: May 3, 1995

[87] PCT Pub. No.: WO94/00434

PCT Pub. Date: Jan. 6, 1994

[30] Foreign Application Priority Data

Jun. 25, 1992 [SE] Sweden .................. 9201956

[51] Int. Cl.$^6$ .................. A61K 31/495; C07D 401/04; C07D 401/14
[52] U.S. Cl. .................. 514/252; 544/364; 544/365
[58] Field of Search .................. 544/365, 364; 514/252

[56] References Cited

U.S. PATENT DOCUMENTS 4,937,245 6/1990 Fex et al. .................. 514/252

OTHER PUBLICATIONS

Drug Evaluations Annual, American Medical Association, 242–243 1993.
Singh et al., Alcohol Drinking in Rats is Attenuated by the Mixed 5-HT1 Agonist / 5-HT2 Antagonist, Alcohol, 10(3), pp. 243–248, published Apr. 28, 1993. Note: Article is currently unavailable to the examiner, so only the abstract is provided Apr. 28, 1993.

*Primary Examiner*—Joseph McKane
*Assistant Examiner*—Richard S. Myers, Jr.
*Attorney, Agent, or Firm*—Birch, Stewart, Kolasch & Birch, LLP

[57] ABSTRACT

Novel compounds of the formula:

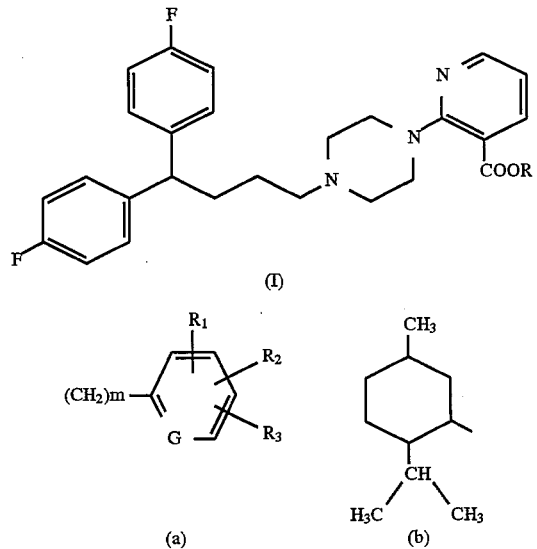

wherein R is selected from saturated or unsaturated alkyls, saturated or unsaturated cycloalkyls, heterocyclic compounds, or from (a) or (b) wherein G is carbon wherein G is carbon or nitrogen; m is 0–10, wherein $R_1$, $R_2$, and $R_3$ are the same or different and selected from hydrogen, halogen, alkyl having 1 to 5 carbon atoms, electron donor groups such as alkoxy having 1–5 carbons or hydroxy, electron acceptor groups selected from cyano, nitro, trifluoroalkyl and the pharmacologically acceptable salts thereof; being useful for treating disorder in the central nervous system.

35 Claims, No Drawings

5,658,910

NICOTINIC ACID ESTERS

This application is a 371 of PCT/SE 93/00565 filed Jun. 23, 1993.

FIELD OF THE INVENTION

The present invention relates to novel bisphenylpiperazine-nicotinic acid esters and acceptable acid salts thereof, to process for the preparation of such compounds as well as new intermediates useful in the preparations of said compounds. Further, the invention relates to pharmaceutical preparations containing the said compounds and the use of said compounds for treatment of mental disorder.

An object of this invention is to provide compounds for therapeutic use, especially compounds having a therapeutic effect via the central nervous system (CNS). An additional object is to provide compounds having an effect on the 5-hydroxytryptamine (5-HT) receptors in meals including man.

PRIOR ART

Various pyridyl- and pyrimidyl derivatives pharmacologically active in the central nervous system are known in the art. Some representative examples can be mentioned. Azaperone, a neuroleptic drug of the butyrophenone series, is a sedative for pigs. Buspirone is an anxiolytic, of which the anxiolytic effect is thought to be mediated via the 5-hydroxytryptamine receptors.

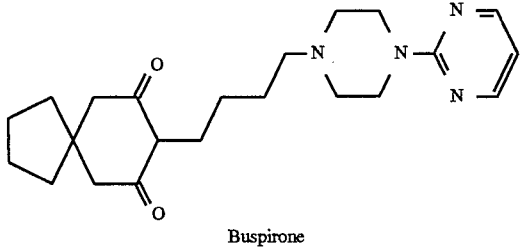

Buspirone

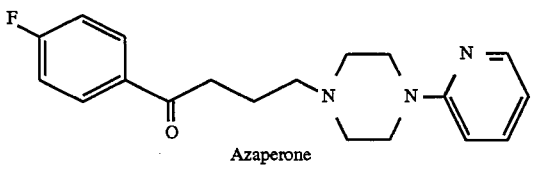

Azaperone

In the U.S. Pat. No. 4,937,245, compounds of the general formula I is disclosed

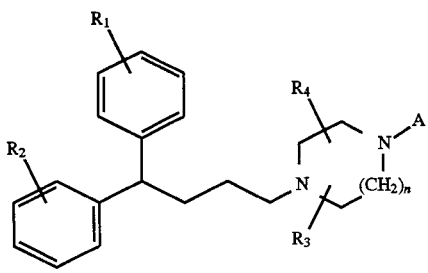

I wherein A is selected from pyridyl or pyrimidyl group, e.g.

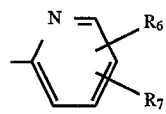

wherein preferably $R_6$ is hydrogen and $R_7$ is cyano, amides, methoxy or hydrogen substituent in the 3-position of the pyridyl ring, useful for the treatment of mental disorders, such as psychoses, depression and anxiety.

DESCRIPTION OF THE INVENTION

The esters of 3-pyridinecarboxylic acid(2-(4-(4,4-bis(4-fluorophenyl)butyl)-1-piperazinyl) of the present invention have unexpectedly been found to show pharmacological properties superior to compounds known in the art.

Thus the present invention provides novel compounds of the general formula (II).

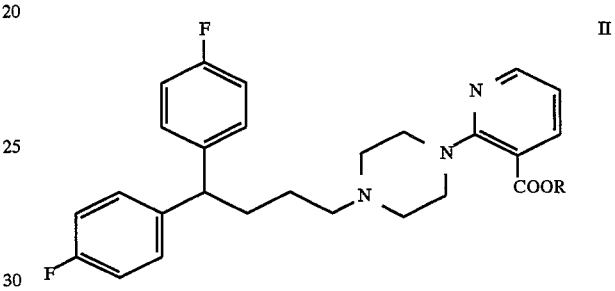

II

R is selected from saturated or unsaturated alkyls, saturated or unsaturated cycloalkyls, heterocyclic compounds or from;

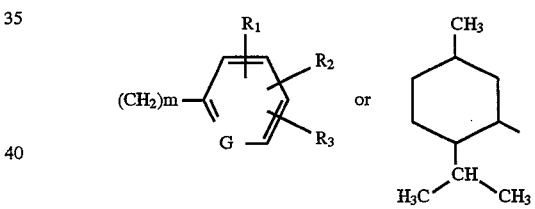

wherein G is carbon or nitrogen;
m is 0–10;
wherein $R_1$, $R_2$ and $R_3$ are the same or different and selected from hydrogen, halogen, alkyl having 1 to 5 carbon atoms, electron donor groups such as alkoxy having 1–5 carbon atoms or hydroxy, electron acceptor groups selected from cyano, nitro, trifluoroalkyl or amide, ($-CONH_2$) and the pharmacologically active salts thereof;
and when used in the foregoing definitions the term alkyl is meant to include straight or branched hydrocarbon groups; the term alkoxy is meant to include straight or branched alkoxy groups;
the term halogen includes fluoro, chloro or bromo.

The compounds of formula (II) have basic properties and, consequently, they may be converted to their therapeutically active acid addition salts by treatment with appropriate acids; inorganic acids such as hydrochloric, hydrobromic, sulphuric, nitric and phosphoric acid, or organic acids such as acetic, propanoic, glycolic, lactic, malonic, succinic, fumaric, tartaric, citric and pamoic acid.

Conversely, the salt form can be converted into the free base form by treatment with alkali.

The compounds of formula (II) and their pharmaceutically acceptable salts have valuable pharmacological properties, making them useful for the treatment of mental disorders such as, psychoses, depression, anxiety, senile dementia, Alzheimer's disease, anorexia and substance abuse disorders.

Stress and anxiety in animals can also be treated.

Clinical studies have lent support to 5-hydroxytrypcamine (5-HT) as being important in the pathogenesis of mental disorders ,such as psychoses, depression, anxiety and substance abuse disorders. Considerable current activities are directed in the discovery of new psycho tropic drugs such as $5\text{-HT}_{1A}$ agonists, e.g., buspirone and ipsapirone, $5\text{-HT}_2$ antagonists e.g. amperozide and ritanserin, 5-HT uptake inhibitors e.g. fluoxetine and paroxetine.

Since $5\text{-HT}_{1A}$ and $5\text{-HT}_2$ receptors have been found to interact functionally, compounds with a combined $5\text{-HT}_{1A}$ agonistic and $5\text{-HT}_2$ antagonistic activity would represent very interesting drugs for the treatment of patients suffering from mental disorders.

The compounds of the present invention show a high affinity for $5\text{-HT}_{1A}$ and $5\text{-HT}_2$ receptors and they have also been found to be potent reuptake inhibitors.

While compounds of the general formula (I) and formula (II) posses high affinity for serotonin $5\text{-HT}_{1A}$ and $5\text{-HT}_2$ receptor subtypes, it has now quite surprisingly been found Chac compounds of the present invention is superior from a safety point of view, rendering them useful in therapy in the central nervous system, especially in the serotonergic system of the brain.

Effective quantities of any of the foregoing pharmacologically active compounds of formula (II) may be administrated to a human being or an animal for therapeutic purposes according to usual routes of administration and in usual forms such as solutions, emulsions, tablets, capsules and patches, in pharmaceutically acceptable carriers and parenterally in the form of sterile solutions. Formulations for parental administration may be in the form of aqueous or non-aqueous isotonic sterile injection solutions or suspensions.

Although very small quantities of active materials of the present invention are effective when minor therapy is involved or in cases of administration to subjects having a relatively low body weight, unit dosages are usually from 0.5 mg upwards, depending on the condition to be treated and the age and weight of the patient as well as the response to the medication.

The unit dose may be from 0.1 to 100 milligrams, preferably from I to 10 milligrams. Daily doses should preferably range from 1 to 50 milligrams. The exact individual dosages as well as daily dosages will, of course be determined according to standard medical principals under the direction of a physician or veterinarian.

METHODS OF PREPARATION

The compounds having the general formula (II) may be prepared by the following methods.

Method 1.

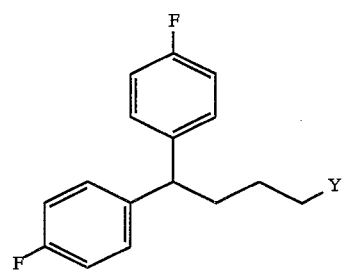

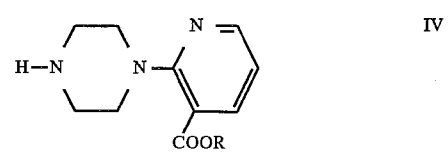

A compound of formula (III), wherein Y is a suitable leaving group such as halogen, alkyl- or arylsulfonate is reacted with a compound of formula (IV), wherein R is as previously defined. The reactions may be carried out using standard N-alkylation procedures.

Method 2.

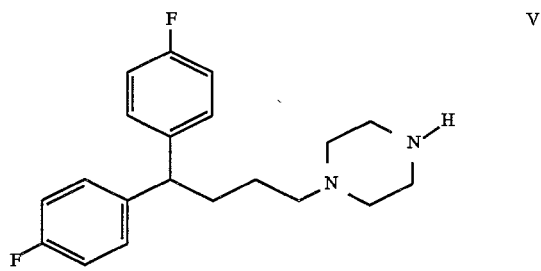

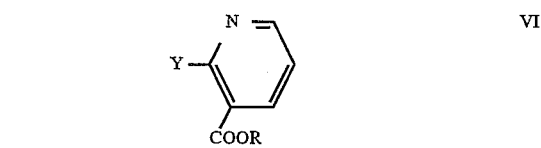

A compound of formula (V) is reacted with a compound (VI) wherein R is as previously defined and y is a leaving group, e.g. halogen.

Method 2b. A method for preparing the intermediate (VI).

Compounds of formula (VI) are prepared in a novel one pot procedure wherein a compound of formula (VII) is reacted with compounds of formula (VIII) wherein R is as previously defined under the catalysis of Lewis acids in dioxane.

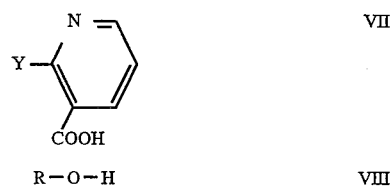

Method 3.

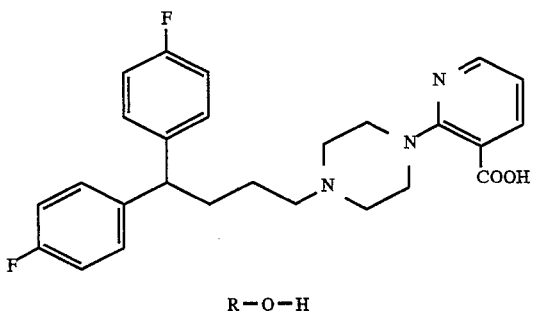

IX

R—O—H  VIII

A compound of formula (IX) is reacted with compounds of formula (VIII) wherein R is as previously defined under the catalysis of a suitable acid in a suitable solvent.

EXAMPLES

The following examples are intended to illustrate but not to limit the scope of the invention, although the compounds named are of particular interest for the intended purposes. These compounds have been designated by a number code, a:b, where a means the number of example, wherein the preparation of the compound is described, and b refers to the order of the compound prepared according to that example. Thus example 1:2 means the second compound prepared according to example 1.

The structures of the compounds are confirmed by IR, NMR, MS and elemental analysis. When melting points are given, these are uncorrected.

Example 1

4-(4.4-Bis(p-fluorophenyl)butyl)-1-(2-(ethyl-pyridine-3-carboxylate)-yl) piperazine hydrochloride 3.3 g (0.01 mole) of 1-chloro-4,4-bis(p-fluorophenyl) butane, 4.42 g (0.02 mole) of 1-(2-(ethyl-pyridine-3-carboxylate)-yl)-piperazine and 0.05 g of KI were fluxed in 30 ml of toluene for 36 hours. After cooling and addition of 45 ml of ether, the solid precipitated was filtered of. After subsequent washing several times with water the organic layer was dried with $Na_2SO_4$. Evaporation of the solvents yielded the crude base. This was dissolved in ether and HCl in ethanol was added to precipitate the hydrochloride. Recrystallisation from EtOAc/EtOH yielded 2.1 g (42%) of the title compound (1:1), m.p. 156°–157° C.

Example 2

3-Pyridinecarboxylic acid (2-(4-(4,4-bis(4-fluorophenyl)butyl)-1-piperazinyl-) ethyl ester hydrochloride 10 g (0.03 mole) of 1-(4,4-bis(p-fluorophenyl)butyl)-piperazine and 5.7 g (0.033 mole) of 2-chloro-(ethyl-pyridine-3-carboxylate) was refluxed in 10 ml of toluene for 16 hours. After cooling to room temperature the reaction mixture was extracted several times and the organic layer was dried over sodium sulphate. Evaporation of the solvents yielded the crude base. The base was dissolved in 11.5 ml of acetone and 7 ml of 5-N HCl was added. The mixture was stirred for 5 minutes and then 28.5 ml of water was added. The mixture was left over night at room temperature and the title compound was crystallised. The yield was 14.9 g (99%) of the title compound (2:1), m.p. 156°–157° C.

In essentially the same way the following compounds were prepared.

2:2 1-[4,4-Bis(p-fluorophenyl)butyl]-4-(3-isopropoxycarbonyl-2-pyridyl)-piperazine, hydrochloride m.p. 155°–156° C.

2:3 1-[4,4-Bis(p-fluorophenyl)butyl]-4-[3-(3-fluorophenoxy)carbonyl-2-pyridyl]-piperazine, hydrochloride m.p. 139°–141° C.

2:4 1-[4,4-Bis(p-fluorophenyl)butyl]-4-(3-methoxycarbonyl-2-pyridyl)-piperazine, hydrochloride m.p. 167°–168° C.

2:5 1-[4,4-Bis(p-fluorophenyl)butyl]-4-(3-benzyloxycarbonyl-2-pyridyl)-piperazine, hydrochloride m.p. 161°–162° C.

2:6 1-[4,4-Bis(p-fluorophenyl)butyl]-4-(3-cyclohexyloxycarbonyl-2-pyridyl)-piperazine, hydrochloride m.p. 155°–156° C.

2:7 1-[4,4-Bis(p-fluorophenyl)butyl]-4-(3-isoamyloxycarbonyl-2-pyridyl)-piperazine, hydrochloride m.p. 150°–151° C.

2:8 1-[4,4-Bis-p-fluorophenyl)butyl]-4-(3-menthoxycarbonyl-2-pyridyl)-piperazine, hydrochloride m.p. 115°–116° C.

2:9 1-[4,4-Bis(p-fluorophenyl)butyl]-4-(3-(1R,2S,5R)-menthoxycarbonyl-2-pyridyl)-piperazine, hydrochloride m.p. 102°–103° C.

2:10 1-[4,4-Bis(p-fluorophenyl)butyl]-4-[3-(2-pyridinylmethoxycarbonyl)-2-pyridyl]-piperazine, hydrochloride m.p. 132°–133° C.

2:11 1-[4,4-Bis(p-fluorophenyl)butyl]-4-(3-1-tert-amyloxycarbonyl-2-pyridyl)-piperazine, hydrochloride m.p. 139°–140° C.

2:12 1-[4,4-Bis(p-fluorophenyl)butyl]-4-(3-cycloocyloxycarbonyl-2-pyridyl)-piperazine, hydrochloride m.p. 183°–184° C.

2:13 1-[4,4-Bis(p-fluorophenyl)butyl]-4-[3-(4-phenyl-2-butyloxycarbonyl)-2-pyridyl]-piperazine, hydrochloride m.p. 96°–98° C.

2:14 1-[4,4-Bis(p-fluorophenyl)butyl]-4-[3-(4-chloro-2-methylphenoxycarbonyl)-2-pyridyl]-piperazine, hydrochloride m.p. 155°–156° C.

2:15 1-[4,4-Bis(p-fluorophenyl)butyl]-4-[3-(4-carboethoxyphenoxycarbonyl)-2-pyridyl]-piperazine, hydrochloride m.p. 182°–183° C.

2:16 1-[4,4-Bis( p-fluorophenyl)butyl]-4-[3-(2,5-dichlorobenzyloxycarbonyl)2-pyridyl]-piperazine, hydrochloride m.p. 131° C.

2:17 1-[4,4-Bis(p-fluorophenyl)butyl]-4-[3-(4-cyanophenoxycarbonyl)-2-pyridyl]-piperazine, hydrochloride m.p.

2:18 1-[4,4-Bis(p-fluorophenyl)butyl]-4-[3-(3-nitrophenoxycarbonyl)-2-pyridyl]-piperazine, hydrochloride m.p.

2:19 1-[4,4-Bis(p-fluorophenyl)butyl]-4-[3-(2-nitrophenoxycarbonyl)-2-pyridyl]-piperazine, hydrochloride m.p.

2:20 1-[4,4-Bis(p-fluorophenyl)butyl]-4-[3-(2-phenylethoxycarbonyl)-2-pyridyl]-piperazine, hydrochloride m.p.

2:21 1-[4,4-Bis(p-fluorophenyl)butyl]-4-[3-(4-bromo-3,5-dimethylphenoxycarbonyl)-2-pyridyl]-piperazine, hydrochloride m.p. 107°–108° C.

2:22 1-[4,4-Bis(p-fluorophenyl)butyl]-4-[3-(3-fluorobenzyloxycarbonyl)-2-pyridyl]-piperazine, hydrochloride m.p. 160°–161° C.

2:23 1-[4,4-Bis(p-fluorophenyl)butyl]-4-[3-(4-carbamylphenoxycarbonyl)-2-pyridyl]-piperazine, hydrochloride m.p.

Example 2b

2-Chloro-(3-pyridinecarboxylic acid) ethyl ester 10 g (0.0635 mole) of 2-chloronicotinic acid, 4.86 ml (0.067 mole) of thionylchloride and 30 ml of dioxane are heated at 70° C. for 3 hours. 20 ml of ethanol is added and the mixture is heated for 2 hours. After cooling to room temperature 10 ml of triethylamine, 10 ml of water and 5 ml ethanol is added. The solvents are evaporated and the residue is extracted with ether and water. The ether is evaporated and the crude product is isolated. The yield is 10.3 g (95%). Distillation of the crude product at 8 mm Bp. 122°–123° C. yielded 9.4 g (90%) of the title compound (2b:1), b.p. 122°–123° C. at 8 mm Hg.

Example 4

This example illustrates the potency of compounds of formula (II) and their therapeutically active acid addition salts for treatment of mental disorders.

Test 1. Affinity for 5HT2-receptors

The binding assay was carried out essentially as described by Leysen et al., (Mol. Pharmcol. 21, 301–314, 1982) using 3 H-kezanserine as ligand.

Test 2. Affinity for 5HT1A-receptors

The binding assay was carried out essentially as described by Peroutka S. J., (Brain Res. 344, 167–171, 1985).

TABLE 1

Affinity for $5HT_2$-receptors

| Compound | Ki(nM) |
|---|---|
| 2:1 | 5.7 |
| 2:4 | 4.0 |
| 2:7 | 2.7 |
| 2:10 | 0.6 |
| 1:17* | inactive |

*From U.S. Pat. No. 4,937,245

TABLE 2

Affinity for $5HT_{1A}$-receptors

| Compound | Ki(nM) |
|---|---|
| 2:1 | 1.2 |
| 2:4 | 0.7 |
| 2:7 | 14 |
| 1:17* | 527 |

*From U.S. Pat. No. 4,937,245

Example 5

The following formulations representative for all of the pharmacologically active compounds of this invention. Example of a suitable capsule formulation:

| | Per capsule |
|---|---|
| Active ingredient, as salt | 5 mg |
| Lactose | 250 mg |
| Starch | 120 mg |
| Magnesium stearate | 5 mg |
| Total | 385 mg |

In case of higher amounts of active ingredient, the amount of lactose used may be reduced.

Example of a suitable tablet formulation:

| | Per tablet |
|---|---|
| Active ingredient, as salt | 5 mg |
| Potato starch | 90 mg |
| Colloidal Silica | 10 mg |
| Talc | 20 mg |
| Magnesium stearate | 2 mg |
| 5% aqueous solution of gelatine | 25 mg |
| Total | 152 mg |

Solutions for parental administration by injection can be prepared in an aqueous solution of a water-soluble pharmaceutically acceptable acid addition salt of the active substance preferably in a concentration of 0.1% to about 5% by weight. These solutions may also contain stabilising agents and/or buffering agents.

We claim:

1. A compound of formula (II):

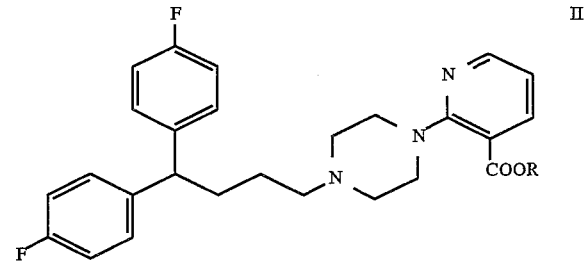

wherein R is a group of the formula

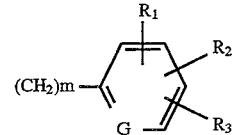

wherein G is carbon or nitrogen;

m is 0–10;

$R_1$, $R_2$ and $R_3$ are the same or different and are selected from the group consisting of hydrogen, halogen, alkyl having 1 to 5 carbon atoms, electron donor groups selected from the group consisting of alkoxy having 1 to 5 carbon atoms and hydroxy, and electron acceptor groups selected from the group consisting of cyano, nitro, trifluoroalkyl, and —$CONH_2$; or a pharmacologically active salt thereof.

2. A pharmaceutical composition comprising, as an active ingredient, one or more of the compounds having the formula (II) as claimed in claim 1, and a pharmaceutically acceptable carrier.

3. A method for treating a mental disorder selected from the group consisting of psychosis, depression, anxiety, senile dementia, Alzheimer's disease, anorexia and substance abuse disorder, which comprises the step of: administering an effective amount of a compound having the formula (II) as claimed in claim 1 or 20 to a patient in need of treatment.

4. A compound of the formula

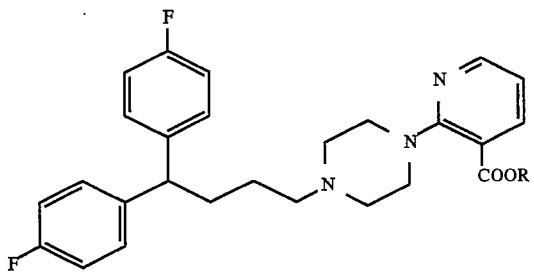

wherein R is a lower alkyl group or a pharmacologically active salt thereof.

5. A compound of the formula

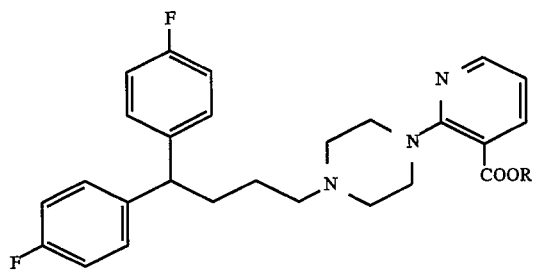

wherein R is a cycloalkyl group or a pharmacologically active salt thereof.

6. The method of claim 3, wherein said mental disorder is a psychosis.

7. The method of claim 3, wherein said mental disorder is depression.

8. The method of claim 3, wherein said mental disorder is anxiety.

9. The method of claim 3, wherein said mental disorder is senile dementia.

10. The method of claim 3, wherein said mental disorder is Alzheimer's disease.

11. The method of claim 3, wherein said mental disorder is anorexia.

12. The method of claim 3, wherein said mental disorder is a substance abuse disorder.

13. The compound of claim 1, which is 1-[4,4-Bis(p-fluorophenyl)butyl]-4-[3-(3-fluorophenoxy) carbonyl-2-pyridyl]-piperazine or a pharmacologically active salt thereof.

14. The compound 1-[4,4-Bis(p-fluorophenyl)butyl]-4-(3-methoxycarbonyl-2-pyridyl)-piperazine or a pharmacologically active salt thereof.

15. The compound of claim 1, which is 1-[4,4-Bis(p-fluorophenyl-) butyl ]-4-(3-benzyloxycarbonyl-2-pyridyl)-piperazine or a pharmacologically active salt thereof.

16. The compound of claim 5, which is 1-[4,4-Bis(p-fluorophenyl)butyl]-4-(3-cyclohexyloxycarbonyl-2-pyridyl)-piperazine or a pharmacologically active salt thereof.

17. The compound of claim 4, which is 1-[4,4-Bis(p-fluorophenyl)butyl]-4-(3-isoamyloxycarbonyl-2-pyridyl)-piperazine or a pharmacologically active salt thereof.

18. The compound 1-[4,4-Bis(p-fluorophenyl)butyl]-4-(3-menthoxycarbonyl-2-pyridyl)-piperazine or a pharmacologically active salt thereof.

19. The compound of claim 18, which is 1-[4,4-Bis(p-fluorophenyl)butyl]-4-(3-(1R, 2 S, 5R)-menthoxycarbonyl-2-pyridyl)-piperazine or a pharmacologically active salt thereof.

20. The compound 1-[4,4-Bis(p-fluorophenyl)butyl]-4-[3-(2-pyridinylmethoxycarbonyl)-2-pyridyl]-piperazine or a pharmacologically active salt thereof.

21. The compound of claim 4, which is 1-[4,4-Bis(p-fluorophenyl)butyl]-4-(3-1-tert-amyloxycarbonyl-2-pyridyl)-piperazine or a pharmacologically active salt thereof.

22. The compound of claim 5, which is 1-[4,4-Bis(p-fluorophenyl)butyl]-4-(3-cyclooctyloxycarbonyl-2-pyridyl)-piperazine or a pharmacologically active salt thereof.

23. The compound of claim 1, which is 1-[4,4-Bis(p-fluorophenyl)butyl]-4-[3-(4-phenyl-2-butyloxycarbonyl)-2-pyridyl]-piperazine or a pharmacologically active salt thereof.

24. The compound of claim 1, which is 1-[4,4-Bis(p-fluorophenyl)butyl]-4-[3-(4-chloro-2-methylphenoxycarbonyl)-2-pyridyl]-piperazine or a pharmacologically active salt thereof.

25. The compound of claim 1, which is 1-[4,4-Bis(p-fluorophenyl)butyl]-4-[3-(4-carboethoxyphenoxycarbonyl)-2-pyridyl]-piperazine or a pharmacologically active salt thereof.

26. The compound of claim 1, which ms 1-[4,4-Bis(p-fluorophenyl)butyl]-4-[3-(2,5-dichlorobenzyloxycarbonyl)-2-pyridyl]-piperazine or a pharmacologically active salt thereof.

27. The compound of claim 1, which is 1-[4,4-Bis(p-fluorophenyl)butyl]-4-[3-(4-cyanophenoxycarbonyl)-2-pyridyl]-piperazine or a pharmacologically active salt thereof.

28. The compound of claim 1, which is 1-[4,4-Bis(p-fluorophenyl)butyl]-4-[3-(3-nitrophenoxycarbonyl)-2-pyridyl]-piperazine or a pharmacologically active salt thereof.

29. The compound of claim 1, which is 1-[4,4-Bis(p-fluorophenyl)butyl]-4-[3-(2-nitrophenoxycarbonyl)-2-pyridyl]-piperazine or a pharmacologically active salt thereof.

30. The compound of claim 1, which is 1-[4,4-Bis(p-fluorophenyl)butyl]-4-[3-(2-phenylethoxycarbonyl)-2-pyridyl]-piperazine or a pharmacologically active salt thereof.

31. The compound of claim 1, which is 1-[4,4-Bis(p-fluorophenyl)butyl]-4-[3-(4-bromo-3,5-dimethylphenoxycarbonyl)-2-pyridyl]-piperazine or a pharmacologically active salt thereof.

32. The compound of claim 1, which is 1-[4,4-Bis(p-fluorophenyl)butyl]-4-[3-(3-fluorobenzyloxycarbonyl)-2-pyridyl]-piperazine or a pharmacologically active salt thereof.

33. The compound of claim 1, which is 1-[4,4-Bis(p-fluorophenyl)butyl]-4-[3-(4-carbamylphenoxycarbonyl)-2-pyridyl]-piperazine or a pharmacologically active salt thereof.

34. The compound of claim 1, wherein G is carbon.

35. The compound of claim 1, wherein G is nitrogen.

* * * * *